(12) United States Patent
Ruiz Diaz et al.

(10) Patent No.: US 8,038,438 B2
(45) Date of Patent: Oct. 18, 2011

(54) TOTALLY ADJUSTABLE BRACKET SYSTEM

(76) Inventors: Roberto Ruiz Diaz, Mexico City (MX); Francisco Javier Marichi Rodriguez, Mexico City (MX)

( * ) Notice: Subject to any disclaimer, the term of this patent is extended or adjusted under 35 U.S.C. 154(b) by 286 days.

(21) Appl. No.: 12/158,638

(22) PCT Filed: Dec. 20, 2006

(86) PCT No.: PCT/MX2006/000152
§ 371 (c)(1),
(2), (4) Date: Aug. 28, 2008

(87) PCT Pub. No.: WO2007/073144
PCT Pub. Date: Jun. 28, 2007

(65) Prior Publication Data
US 2010/0003632 A1  Jan. 7, 2010

(30) Foreign Application Priority Data
Dec. 21, 2005 (MX) .................. PA/A/2005/014181

(51) Int. Cl.
*A61C 3/00* (2006.01)
(52) U.S. Cl. ............................. 433/11; 433/9
(58) Field of Classification Search ................ 433/8–17; 29/896.11
See application file for complete search history.

(56) References Cited

U.S. PATENT DOCUMENTS

| | | | |
|---|---|---|---|
| 2,959,857 A | 11/1960 | Stoll | |
| 3,439,421 A | 4/1969 | Perkowski | |
| 3,452,177 A | 6/1969 | Davis et al. | |
| 3,775,850 A * | 12/1973 | Northcutt | 433/16 |
| 4,083,114 A | 4/1978 | Acevedo | |
| 4,209,906 A | 7/1980 | Fujita | |
| 4,243,387 A * | 1/1981 | Prins | 433/16 |
| 4,256,455 A | 3/1981 | Foerster et al. | |
| 4,597,739 A * | 7/1986 | Rosenberg | 433/16 |
| 4,878,840 A * | 11/1989 | Reynolds | 433/9 |
| 5,018,259 A * | 5/1991 | Wildman | 29/896.11 |
| 5,219,282 A | 6/1993 | Lavin | |
| 5,616,026 A * | 4/1997 | Cash | 433/8 |
| 5,711,666 A | 1/1998 | Hanson | |
| 5,879,158 A * | 3/1999 | Doyle et al. | 433/24 |
| 6,071,118 A * | 6/2000 | Damon | 433/9 |
| 6,371,760 B1 | 4/2002 | Zavilenski et al. | |
| 2002/0028417 A1* | 3/2002 | Chapoulaud et al. | 433/24 |
| 2002/0098460 A1* | 7/2002 | Farzin-Nia et al. | 433/13 |
| 2005/0003324 A1 | 1/2005 | Reising | |

FOREIGN PATENT DOCUMENTS

| | | |
|---|---|---|
| EP | 0 285 418 A2 | 10/1988 |
| EP | 0 702 939 A2 | 3/1996 |
| EP | 0 780 101 A2 | 6/1997 |
| EP | 1723927 A1 | 11/2006 |
| WO | WO 99/40871 A1 | 8/1999 |
| WO | WO 2004052229 A2 | 6/2004 |
| WO | WO 2005067810 A1 | 7/2005 |

* cited by examiner

*Primary Examiner* — John J Wilson

(74) *Attorney, Agent, or Firm* — Reinhart Boerner Van Deuren P.C.

(57) ABSTRACT

This invention refers to a totally adjustable, low-friction bracket system which allows the programming of the prescription in an individualized fashion reducing the quantity of adjustments in the archwires, in order to bring the teeth into their suitable positions in orthodontic treatments.

23 Claims, 10 Drawing Sheets

TOTALLY ADJUSTABLE BRACKET SYSTEM

CROSS-REFERENCE TO RELATED PATENT APPLICATIONS

Figure 1:
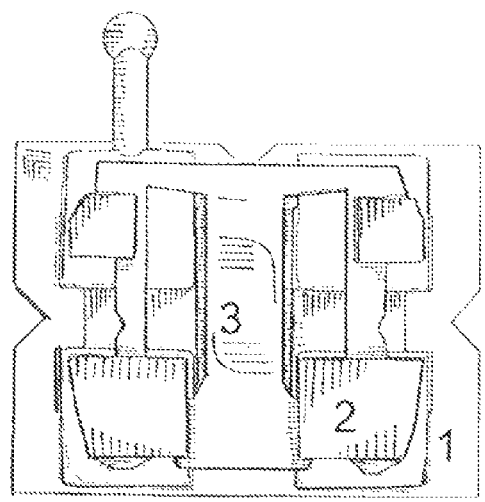

This patent application is the National Stage of International Application No. PCT/MX2006/000152, filed Dec. 20, 2006, that claims priority to Mexican Application No. PA/a/2005/014181, filed Dec. 21, 2005, the entire teachings and disclosure of which are incorporated herein by reference thereto.

The present invention refers to a system of improved brackets applied in orthodontic treatments and whose function is to control the tooth movement in every treatment requiring fixed appliances.

This new design of brackets fits to any available philosophy and treatment mechanics, but the brackets are mainly designed to adapt to the characteristics of each person, individualizing the bracket prescription.

The brackets may be manufactured in stainless steel among other alloys. The brackets consist of three parts: a base, a body and a self-ligating clasp. The base has a mesh in one of its surfaces for bonding to tooth enamel, and in the other one it has a concavity where the body articulates. The body has a convex surface articulating to the base concavity, and the other surface has a slot for inserting the archwires, and four retention wings for ligature holding, each wing having grooves to insert the self-ligating clasp, this clasp is placed within the grooves and its function is ligating the archwire to the bracket.

The field of action of this invention is in dentistry, especially in the orthodontic area for the treatment of malocclusions by means of fixed appliances, that is to say, for tooth alignment in persons with crowded teeth. Different kinds of brackets with different prescriptions are currently available. The aim is to help place the teeth in more suitable positions; however, not everybody has the same characteristics in regard to the tooth inclination, and in order to achieve the final position of the teeth, necessary adjustments are required in the archwires.

That is why, with this invention, the need to bend the archwires is eliminated in order to place the teeth in the appropriate positions according to the needs of each individual, on account of which the bracket prescription may be adjusted tridimensionally, controlling the first, second and third order movements, having the possibility of overtreating the pre-programmed information in the brackets in the cases where it is needed.

This new design allows the prescription of the appliance to be customized to each individual and ensures that only qualified personnel in the orthodontic area is able to use it. Furthermore it is compatible with any available philosophy and treatment mechanics, fitting to the aims of each one of them; it displays the modality that the brackets may be ligated to the archwire in the traditional way (metallic or elastic ligature) or by means of a self-ligating system, improving the working times and decreasing the friction generated during the tooth movement between the archwire and the bracket.

BACKGROUND TO THE INVENTION

At the beginning of the 20$^{th}$ century the need to have a tridimensional control of the tooth movement in orthodontic treatments was visualized. That is why the first brackets were developed. These were attached to the teeth by means of bands which in turn were bonded to the teeth; these first designs, in which the slot was perpendicular to the bracket base, assumed the inclination of the teeth; therefore, the clinicians had to bend the archwires in order to compensate the different inclinations presented by the slots, so the orthodontic treatments were totally craftsmanlike. In the early 1970's, the bracket fastening system to the teeth was changed, and a mesh was added to the base for the direct bonding to the enamel, thus eliminating the need to use bands. In the same decade the first system of preadjusted brackets was developed, these brackets already presented a prescription developed by measuring the inclination presented by the tooth labial (external) surface; from then on, the development of numerous preadjusted systems was started, each one with a different prescription, but with the same aim of placing the teeth in suitable positions without the need to perform bendings in the archwires, which nowadays is known to be wrong, because there are many aspects making persons different from each other. Nowadays clinicians are forced by this situation to make bends in the archwires in order to achieve the tooth positions suitable to each individual.

All of the preadjusted systems initially designed and still prevailing have control of the 1$^{st}$, 2$^{nd}$ and 3$^{rd}$ order movements; the first order-movement control is achieved by modifying the bracket base thickness, the second order-movement control is achieved by inclining the bracket body in relation to the base in the mesio-distal sense, the third order movements are achieved in two ways: 1) inclining the base in relation to the body (torque in the base) and 2) by the inclination of the slot inside the bracket body (torque in the face). This should force the clinicians to have a very precise clinical view. That is why, and in order to avoid those drawbacks, we developed a novel totally adjustable bracket fitting to the dental characteristics of each individual.

DESCRIPTION OF THE INVENTION

Figure 2:
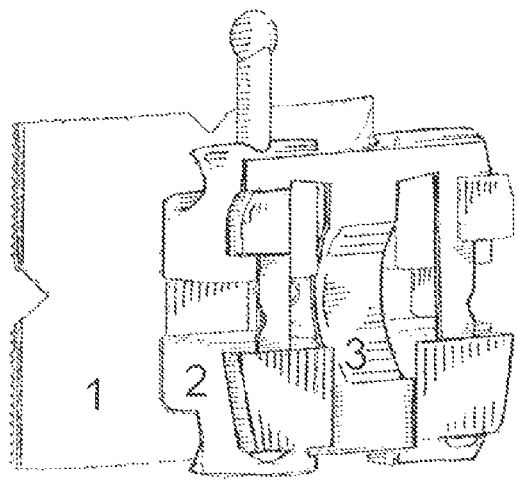
Figure 3:
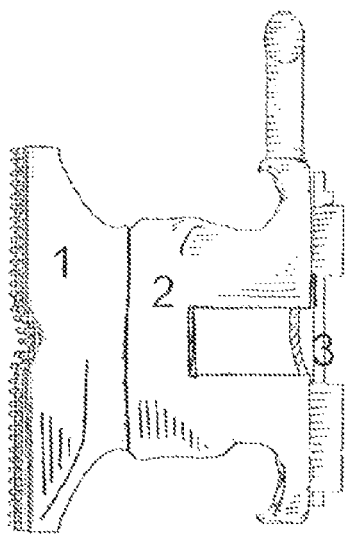
Figure 4:
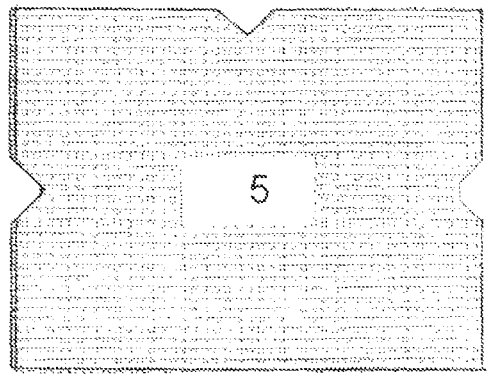
Figure 5:
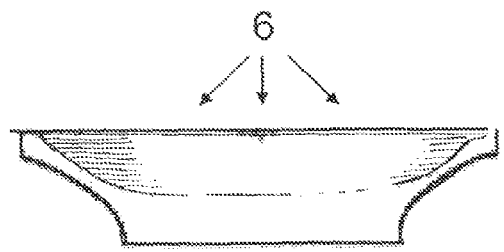
Figure 6:
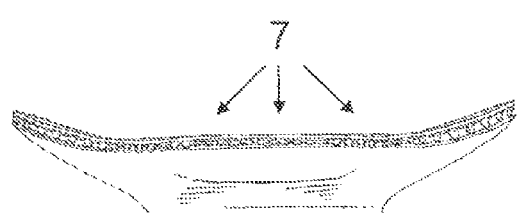
Figure 7:
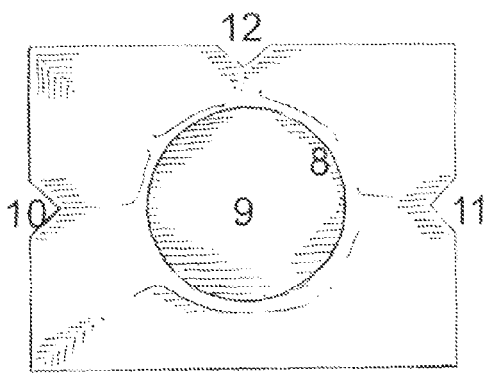
Figure 8:
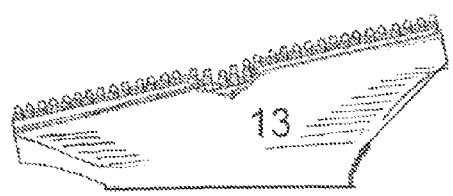
Figure 9:
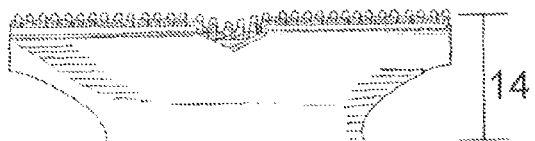
Figure 10:
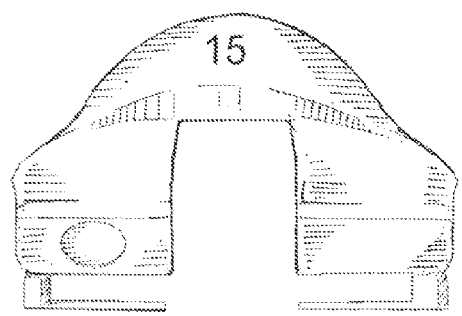
Figure 11:
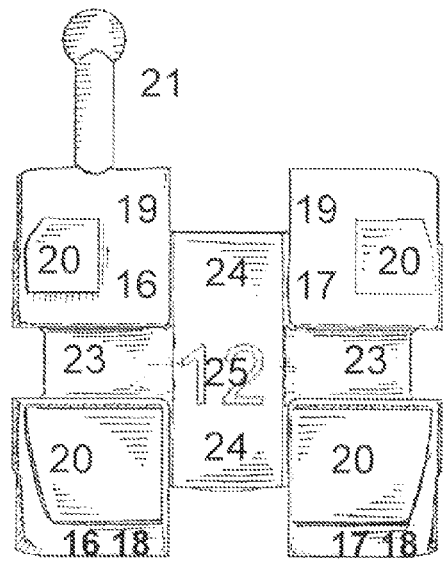
Figure 12:
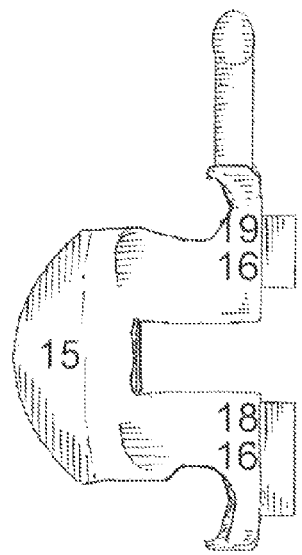
Figure 17:
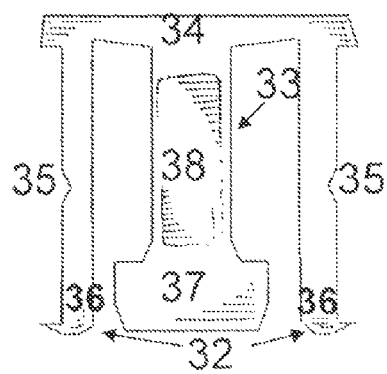
Figure 18:
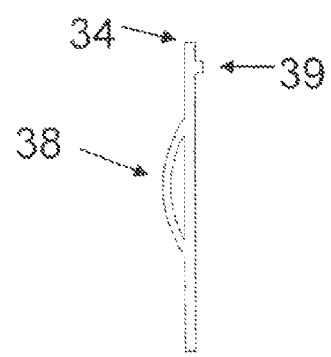
Figure 19:
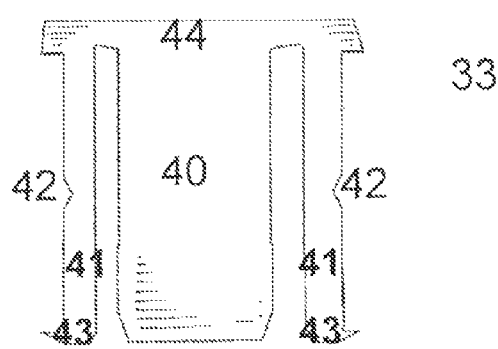
Figure 20:
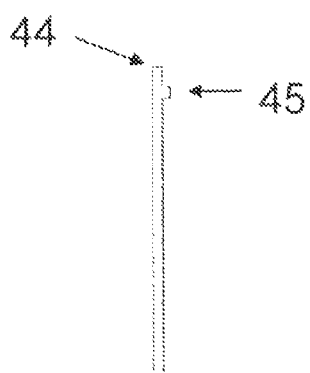
Figure 21A:
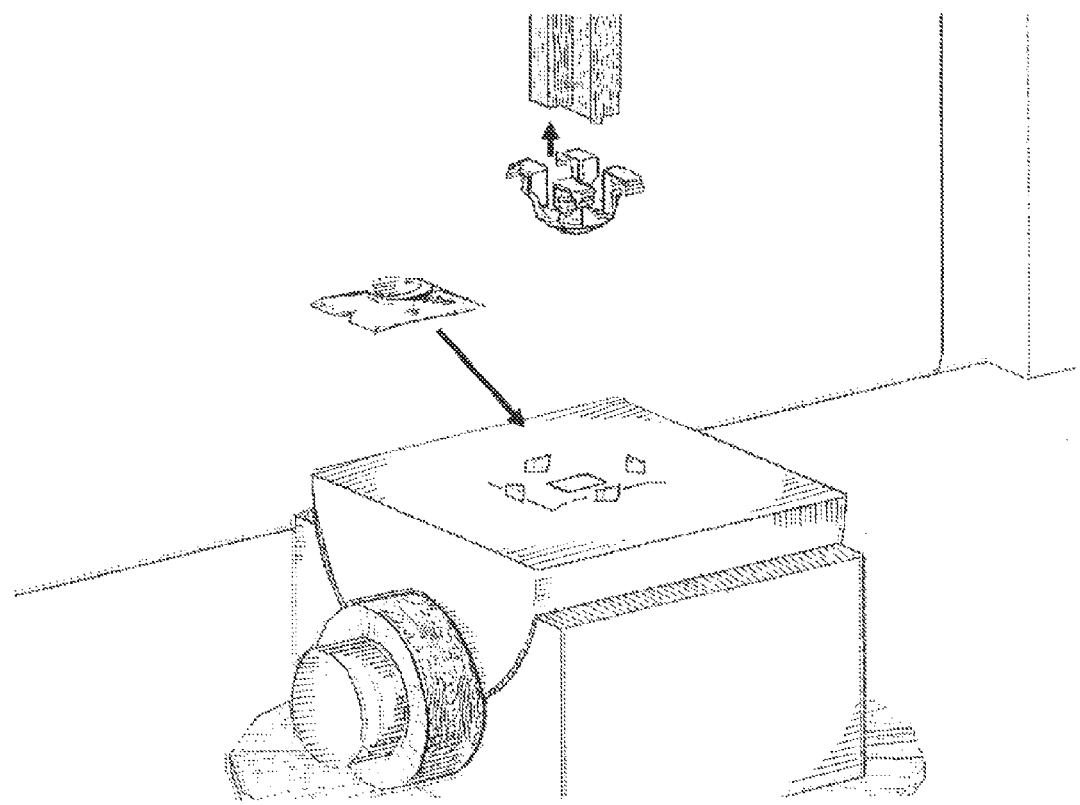
Figure 21B:
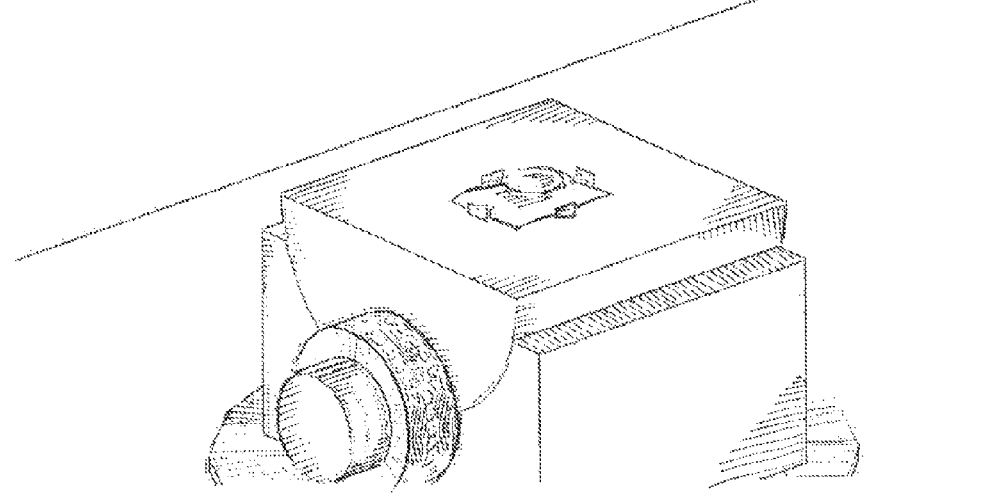
Figure 22A:
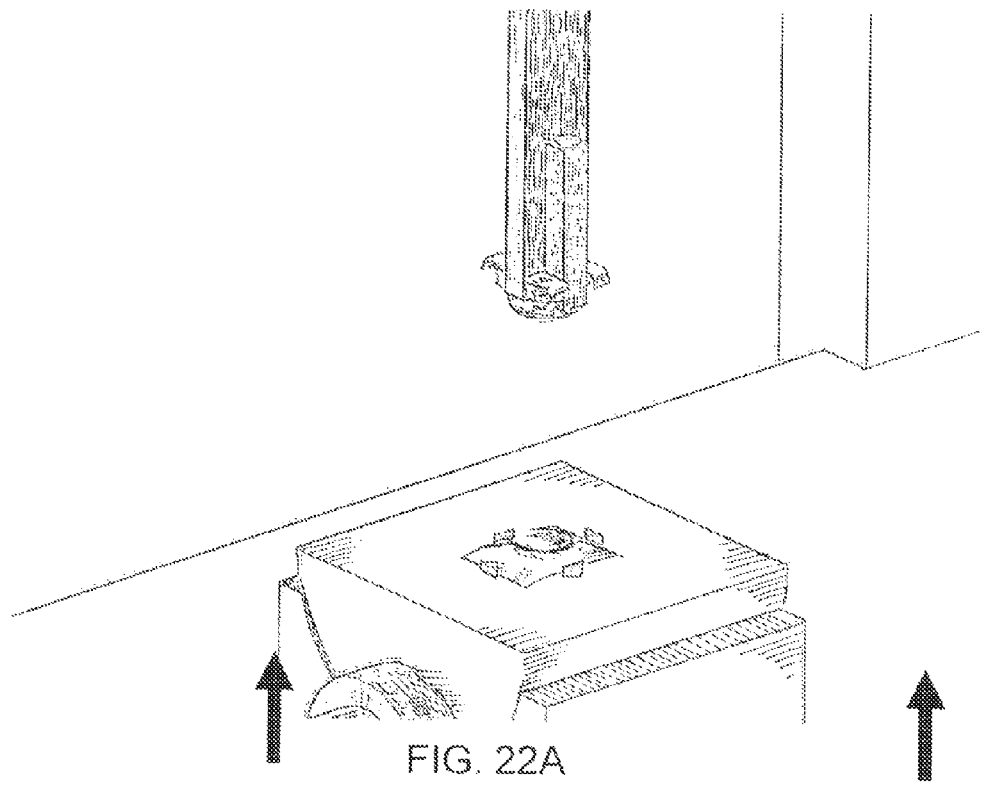
Figure 22B:
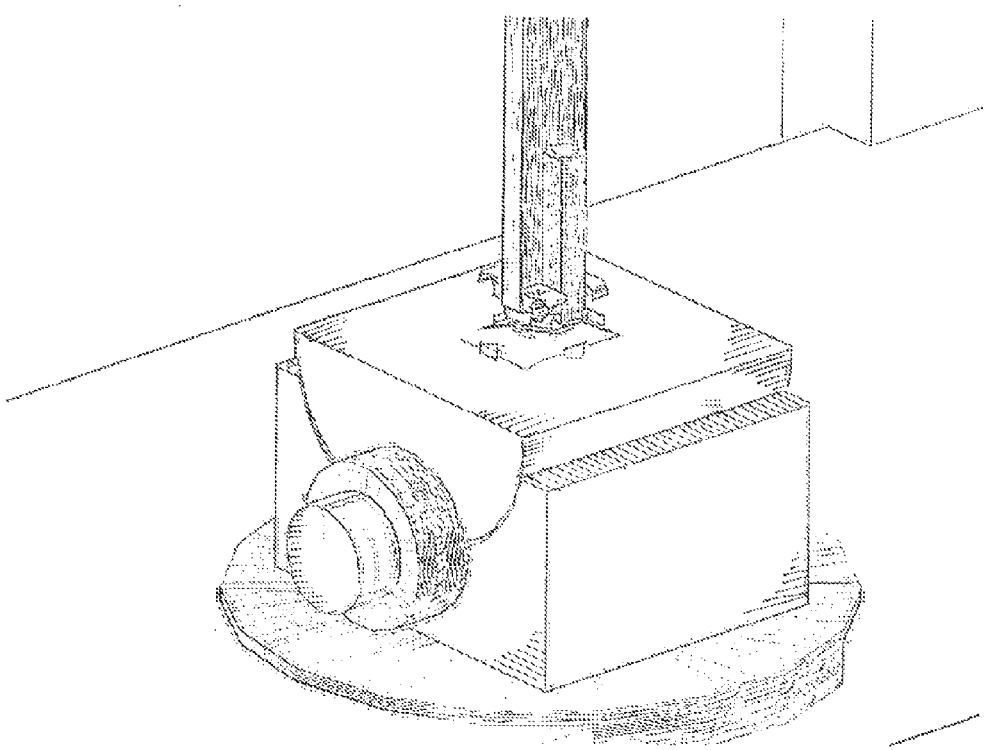
Figure 23A:
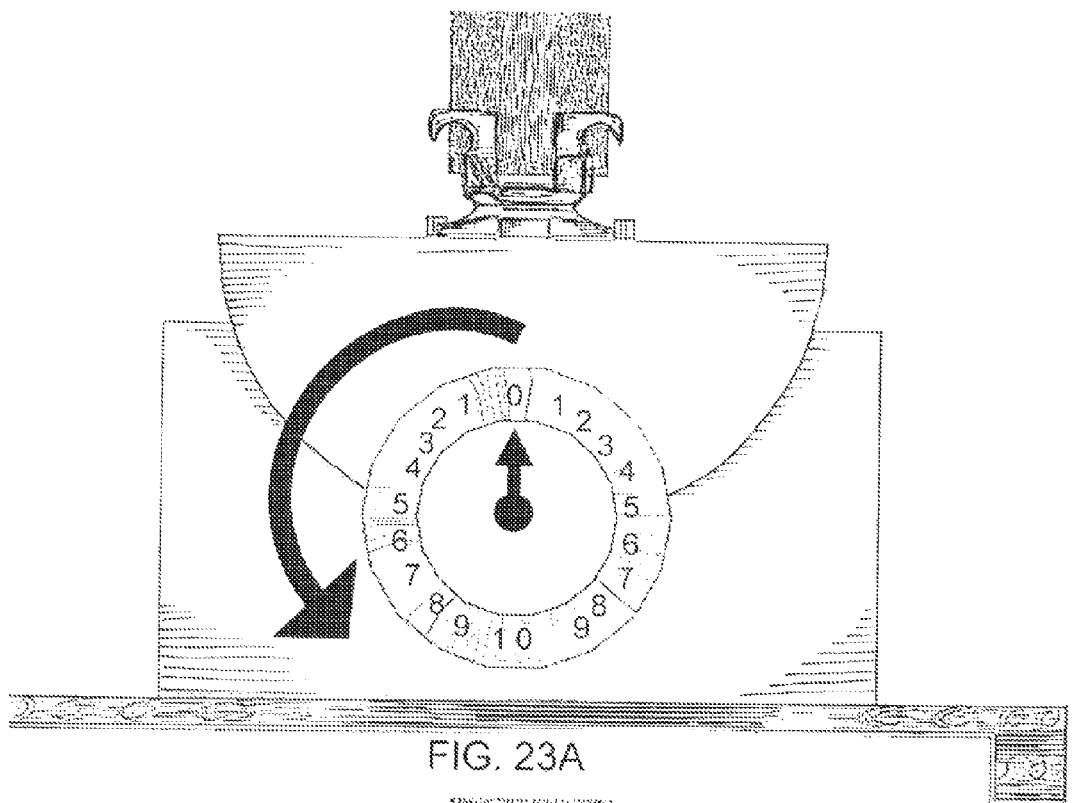
Figure 23B:
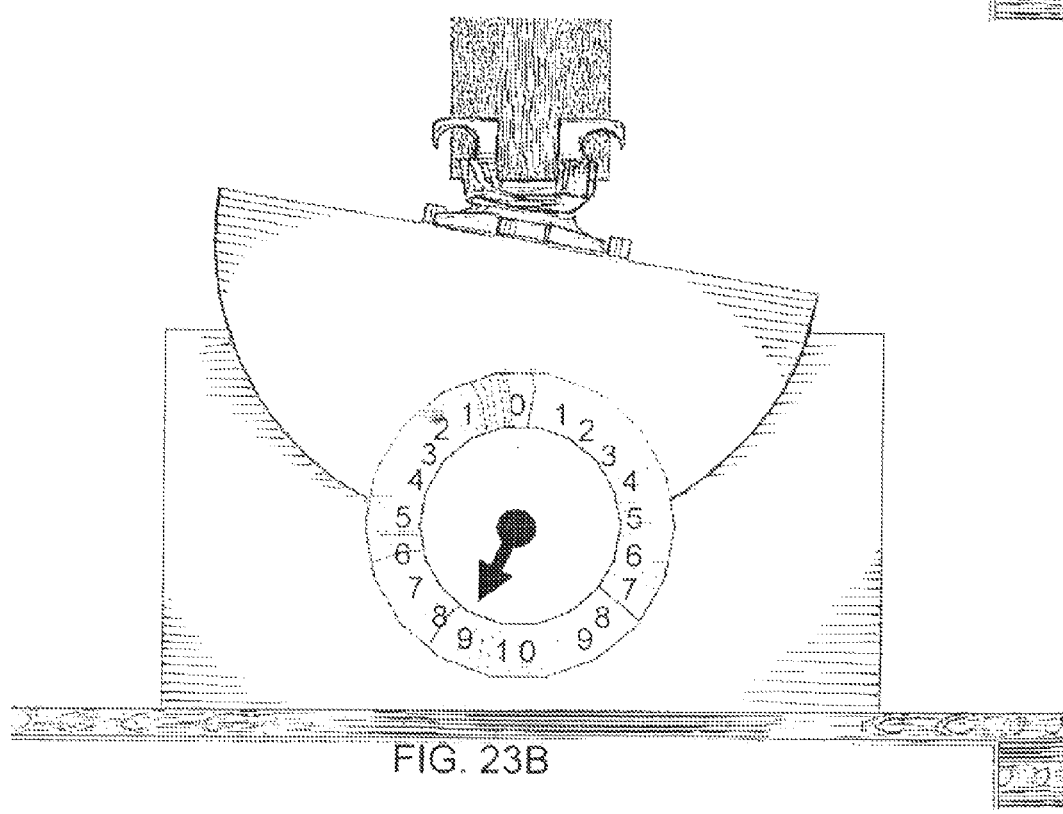
Figure 24A:
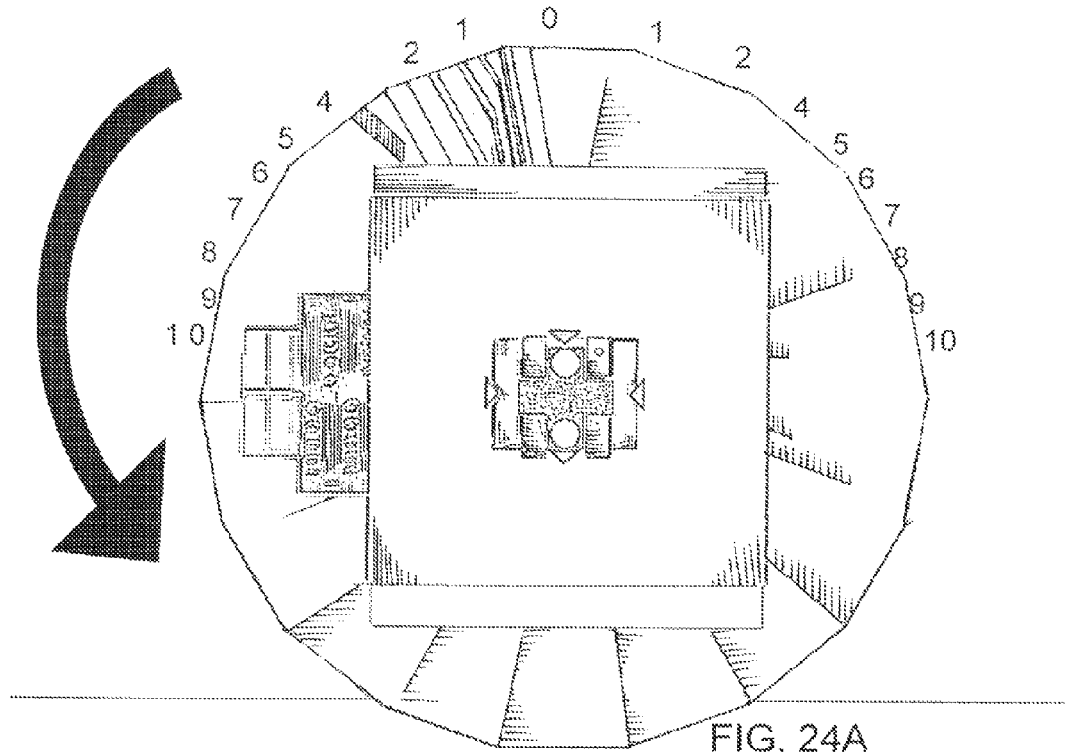
Figure 24B:
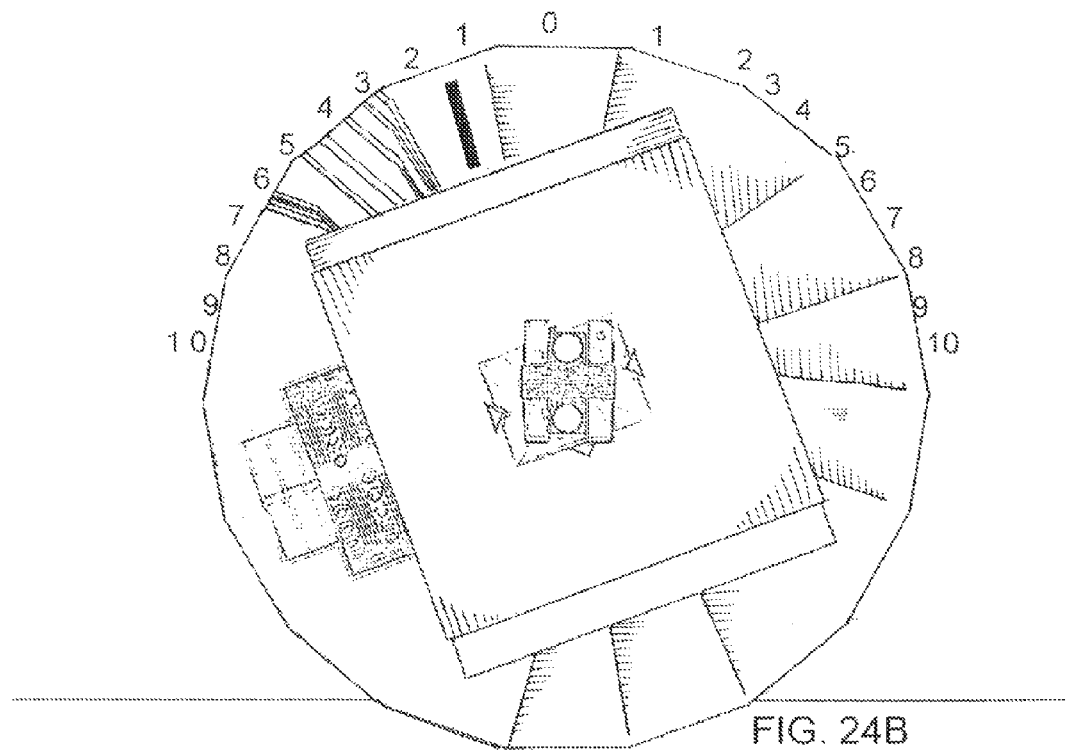
Figure 25A:
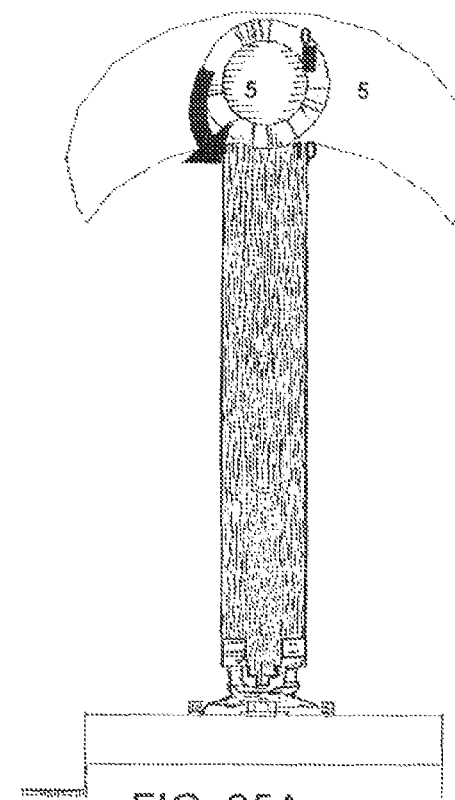
Figure 25B:
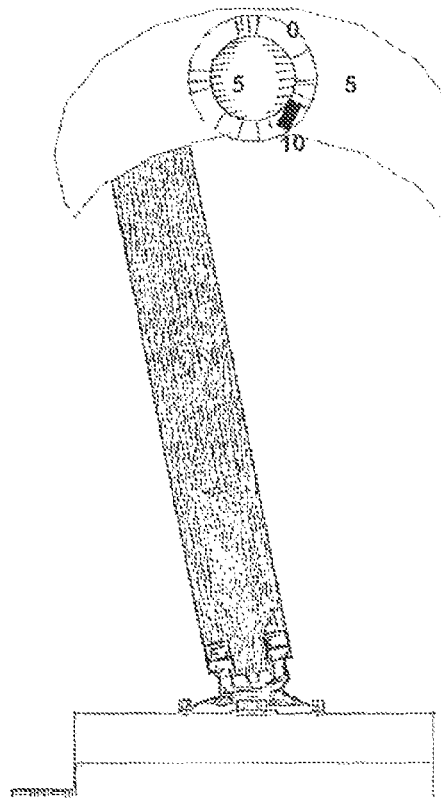

The following description and the accompanying figures clearly show the characteristic details of this novel bracket:
FIG. 1. a Labial view of the bracket
FIG. 2. The bracket viewed in perspective
FIG. 3. Mesiodistal view of the bracket
FIG. 4. Lingual view of the base
FIG. 5. Gingival view of a flat base
FIG. 6. Occlusal view of a curved base
FIG. 7. Labial view of the base
FIG. 8. Mesiodistal view of the base
FIG. 9. Mesiodistal view of the base thickness
FIG. 10. Gingivo-occlusal view of the body
FIG. 11. Labial view of the body
FIG. 12. Mesiodistal view of the body
FIG. 13. Labial view of the bracket without clasp
FIG. 14. Labial view of the bracket with clasp
FIG. 15. Labial view of the low-friction clasp
FIG. 16. Mesiodistal view of the low-friction clasp
FIG. 17. Labial view of the prescription-expression clasp
FIG. 18. Mesiodistal view of the prescription-expression clasp
FIG. 19. Labial view of the esthetic clasp
FIG. 20. Mesiodistal view of the esthetic clasp
FIG. 21a, b. View of the base and body placement in a welding machine
FIG. 22a, b. View of the joining of base and body
FIG. 23a, b. View of torque adjustment in a welding machine
FIG. 24a, b. View of angulation adjustment in a welding machine
FIG. 25a, b. View of anti-rotation adjustment in a welding machine The bracket: Among other alloys, it may be manufactured with stainless steel and consists of three separated parts (FIGS. 1, 2 and 3); a base (1), a body (2) and a self-ligating clasp (3) ready to be joined. Each part displays six surfaces: lingual, labial, mesial, distal, gingival and occlusal.

The base: On its lingual surface (FIG. 4) it displays a mesh for bonding to the enamel (4), the center of this surface shows a rectangular retentive depression designed to receive one of the welding machine points (5), the base lingual surface may be flat (FIG. 5) (6) or concave (FIG. 6) (7) depending on the tooth where it will be placed. The base labial surface (FIG. 7) shows a central concavity, designed to articulate and join to the lingual surface of the body (8); within the concavity silver solder may be added (9) to seal the joint when the base is attached to the body by electrical spot welding. On its mesial (10), distal (11) and gingival (12) ends the base has three indentations for identifying and for holding to the spot welding machine. The base width dimensions vary depending on the tooth where the base is going to be placed. In a mesiodistal view (FIG. 8) the base has an inclination representing the torque prescription in the base which is different for each tooth (13). The base thickness (FIG. 9) may vary depending on the tooth where it will be placed (14), modifying the tooth position in the labial-lingual sense.

The body: Its lingual surface has a convex shape (FIG. 10) (15) for articulating and joining to the concavity on the base labial surface (8); this allows to have ten degrees of rotation in the occluso-gingival sense (torque), ten degrees clockwise or counterclockwise (angulation), and five degrees of rotation in the mesio-distal sense (anti-rotation). On its labial surface the body has two pairs of retentive wings (FIG. 11) which may be used to place elastic chains or metallic ligatures. Each pair of wings is located on mesial (16) and distal (17) of the body, and the wings in each pair show an occlusal (18) and gingival disposition (19). On its labial portion each wing has a groove (20) for the insertion of the self-ligating clasp. Hooks for holding elastics may be added to the gingival wings (21), as well as an identifying mark on the distogingival wing (22). In the space between the wings of each pair, in the occlusogingival sense, there is a horizontal slot of rectangular shape spanning from mesial to distal of the body (23). The slot dimensions are 0.02235×0.028", and it is used to insert principal archwires. In the space between the mesial and distal pairs of wings there is a vertical slot (24) deeper than the horizontal one, used for the insertion of one of the welding device points in order to join the bracket body with the base. The center of the vertical slot shows an identifying number in order to determine the tooth corresponding to the bracket (25). In a mesiodistal view (FIG. 12) the convex shape of the lingual surface is observed (15), as well as the retentive shape of the wings (16, 18, 19).

Figure 13:
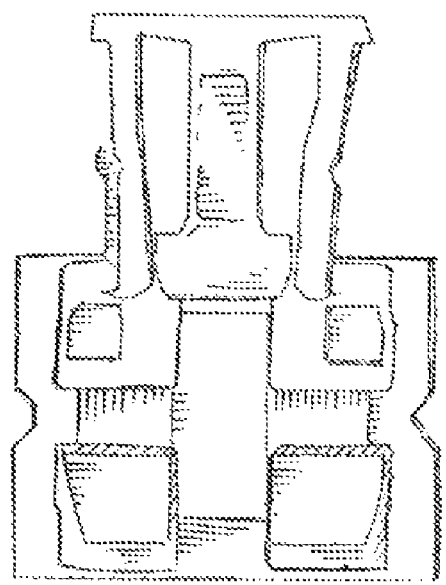
Figure 14:
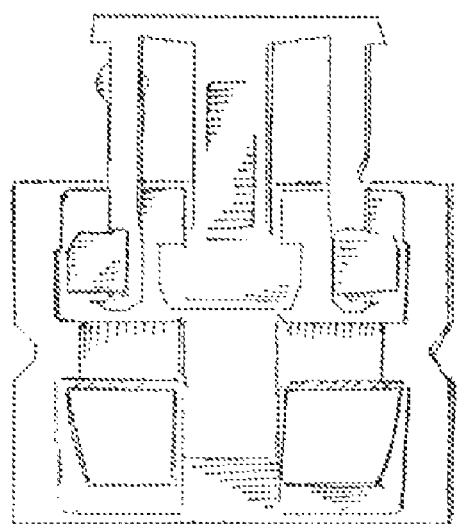
Figure 15:
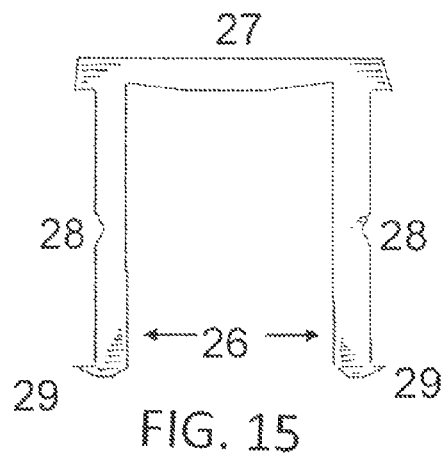
Figure 16:
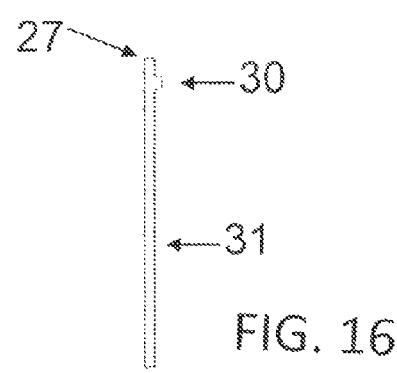

The self-ligating clasp: This moving element is inserted in the grooves that the wings have on their labial surface (20). The clasp is introduced in a gingivo-occlusal direction (FIGS. 13 and 14). This accessory shows a novel dual system which the clinician may place and remove at will. It is designed for use in low-friction mechanics, or for use in the traditional ligating system. The clasp is presented in three modalities: 1) low-friction clasp (FIG. 15), with two parallel arms (26) and a connector (27). The arms have indentations (28) on their mesial and distal surfaces aimed at holding the clasp on insertion and removal. In a mesiodistal view the arms display a groove (29) on their ends to prevent them from being dislodged (FIG. 16).

The connector (27) shows a thickening (30) serving as a stop when the clasp is inserted in the grooves, this clasp by being totally flat (31) allows the slot space to remain free. 2) Prescription-expression clasp (FIG. 17), showing three arms: two lateral arms (32), one inner arm (33) and a connector (34); the lateral arms display indentations (35) aimed at holding the clasp when it is inserted and removed. These arms have grooves on their ends (36) to avoid dislodgement. The inner arm has an irregular shape being wider in its free end (37); this provides more supporting surface to the arm. The center of these arms shows a curvature towards lingual (38) which forces the archwires to seat on the horizontal slot bottom (23). This feature allows the bracket prescription to be expressed by using full size archwires. In a mesiodistal view (FIG. 18), the connector (34) shows a thickening (39) which serves as a stop when the clasp is inserted in the grooves. In this view the curvature of the inner arm towards lingual is observed (38). 3) Esthetic clasp (FIG. 19), this clasp has the modality of a wider and flatter inner arm (4). The lateral arms (41) display indentations (42) serving as a hold for the clasp when it is inserted and removed. On their ends the lateral arms show a groove (43) to prevent them from being dislodged. The connector (44) joins the lateral arms to the inner one. In a mesiodistal view (FIG. 20) the connector (44) shows a thickening (45) serving as a stop when the clasp is inserted in the grooves. This clasp may be manufactured in materials allowing it to have different colors: ivory-colored for adult patients and in color for young patients This totally adjustable bracket system works as follows: all of the brackets have a predetermined prescription of inclination, angulation and movement of first order which the clinician will be able to modify at will by means of the measuring and perspective prescription appliance, whose patent is being taken out. Once the inclination of the tooth labial surface is obtained, including molars, the information is carried to the brackets by means of the welding unit that permits joining the base to the body (FIG. 21a, b); when the base and the body are placed on the welding unit (FIG. 22a, b), the torque is adjusted having the possibility of incrementing or decreasing it up to ten degrees (FIG. 23a, b); following this the angulation is adjusted (FIG. 24a, b) having the possibility of increasing or decreasing it up to ten degrees; an anti-rotation movement of up to five degrees may be added (FIG. 25a, b); the adjustment for the first order movement is achieved by using different base thicknesses.

The brackets may be placed by means of indirect bonding once they have the individualized prescription; the self-ligating clasp modality allows their use in order to generate low friction during the tooth movement, or to use them with a different esthetic appearance, or when there is a need to allow the expression of the prescription by inserting full size archwires, it also allows to place metallic or elastic ligature.

The above-mentioned features eliminate the need to perform adjustments in the archwires, so the orthodontist really would be able to work with straight archwire systems; however, the most important thing of this invention is that it fits to the individual characteristics of the person.

We claim:

1. A system of adjustable brackets which can be tridimensionally adjusted; each bracket has information of angulation, inclination and rotation; characterized by the brackets including: a base with a lingual surface and a labial surface, the labial surface shows a central cavity; the base presents indentations on its ends for identification and holding in a welding machine; furthermore this base has an inclination representing the basic prescription of torque in the base;

a body comprising a labial surface and a lingual surface with a convex shape to articulate and join to the cavity on the labial surface of the base, allowing the free movement of the body on the base in order to modify the basic prescription to a desired value; this body on its labial portion has a space and two pairs of wings for the placement of holding elements;

and a self-ligating clasp which can be removeably inserted in the body of the bracket; and wherein the self-ligating clasp being a low-friction clasp which comprises two parallel arms and a connector joining the arms; on their mesial and distal surface these arms display indentations serving as a hold for the clasp when its inserted in, and removed from, the bracket body; furthermore on their ends these arms have a groove avoiding their dislodgement from the body; the connector has a thickening serving as a stop when the clasp is inserted in the grooves.

2. A system of adjustable brackets according to claim 1, wherein the low-friction clasp being flat, which allows the slot space to remain free.

3. A system of adjustable brackets which can be tridimensionally adjusted; each bracket has information of angulation, inclination and rotation; characterized by the brackets including: a base with a lingual surface and a labial surface, the labial surface shows a central cavity; the base presents indentations on its ends for identification and holding in a welding machine; furthermore this base has an inclination representing the basic prescription of torque in the base;

a body comprising a labial surface and a lingual surface with a convex shape to articulate and join to the cavity on the labial surface of the base, allowing the free movement of the body on the base in order to modify the basic prescription to a desired value; this body on its labial portion has a space and two pairs of wings for the placement of holding elements;

and a self-ligating clasp which can be removeably inserted in the body of the bracket; and wherein the self-ligating clasp being a prescription-expressing clasp which includes three arms: two lateral arms and an inner arm, as well as a connector joining the lateral arms to the inner one; on the mesial and distal surfaces the lateral arms display indentations serving as a hold for the clasp on its insertion in, and removal from, the bracket body; furthermore on their ends these lateral arms have a groove which prevents them from being dislodged from the body; this inner arm has an irregular shape being wider on its free end, in order to enter in the lower grooves of the bracket to avoid tilting; this connector has a thickening serving as a stop when the clasp is inserted in the grooves.

4. A system of adjustable brackets according to claim 3, wherein the prescription-expressing clasp having in the middle portion of its inner arm, a curvature toward the lingual surface that forces an archwire to seat on the bottom of the slot, thus allowing the expression of the bracket prescription by using full size archwires.

5. A system of adjustable brackets which can be tridimensionally adjusted; each bracket has information of angulation, inclination and rotation; characterized by the brackets including: a base with a lingual surface and a labial surface, the labial surface shows a central cavity; the base presents indentations on its ends for identification and holding in a welding machine; furthermore this base has an inclination representing the basic prescription of torque in the base;

a body comprising a labial surface and a lingual surface with a convex shape to articulate and join to the cavity on the labial surface of the base, allowing the free movement of the body on the base in order to modify the basic prescription to a desired value; this body on its labial portion has a space and two pairs of wings for the placement of holding elements;

and a self-ligating clasp which can be removeably inserted in the body of the bracket; and wherein the self-ligating clasp being an esthetic clasp which includes three arms, two lateral arms and an inner arm, the inner one being wider; on their mesial and distal surfaces the lateral arms display indentations serving as a hold for the clasp when it is inserted in, and removed from, the bracket body, furthermore on their ends this lateral arms have a groove which prevents their dislodgement from the body; a connector joining the lateral arms to the inner one, this connector has a thickening serving as a stop when the clasp is inserted in the grooves.

6. A system of adjustable brackets according to claim 5, wherein the esthetic clasp having the possibility of being manufactured in materials allowing the application of some color.

7. A system of adjustable brackets comprising:

a plurality of brackets where the bracket prescription can be three-dimensionally programmed according to the characteristics obtained from each tooth of a person by individualizing the bracket prescription by varying the angulation, inclination and rotation for each bracket based on the characteristics of the corresponding tooth as needed;

wherein at least one bracket comprises:

a base with a lingual surface and a labial surface, a central cavity in the labial surface defining a contact surface; furthermore this base has an inclination representing the basic prescription of torque in the base according to each tooth;

a body comprising a labial surface and a lingual surface with a convex shape defining a contact surface to articulate and join to the cavity on the labial surface of the base;

wherein a full free movement of the body on the base can be obtained in all the contact surface of the body and in all the contact surface of the base in order to program the bracket prescription required for each tooth to a desired value, where the base and the body will be fixed making a single piece in accordance with the prescription obtained from each patient tooth;

wherein the cavity of the base and the convexity of the body generate a ball-and-socket type joint, which allows the adjustment of the bracket prescription before welding, permitting the orientation of the body in any desired direction;

wherein the body on a portion of the labial surface has a slot and two pairs of wings for the placement of holding elements;

wherein the body additionally includes a slot for the insertion of archwires, which is adjusted to a position depending on the body orientation;

wherein the bracket body additionally includes a hook for holding elastic accessories;

further including a self-ligating clasp which can be removably inserted in the body of the bracket;

wherein the wings of the bracket body further include grooves on the labial portion, the grooves defining the space on the labial portion of the bracket body, where the self-ligating clasp can be inserted; and wherein the self-ligating clasp comprises two parallel arms and a connector joining the arms; on their mesial and distal surface, the arms display indentations serving as a hold for the clasp when it is inserted in, and removed from, the bracket body; the arms have a groove on their ends that avoids their dislodgement from the body; the connector has a thickening that serves as a stop when the clasp is inserted in the grooves.

8. The system of adjustable brackets according to claim 7, wherein the fixing of the body to the base is carried out by welding.

9. The system of adjustable brackets according to claim 8, wherein the welding is by electric welding.

10. The system of adjustable brackets according to claim 9, wherein the base has a cavity on its lingual surface for the insertion of an electrode of a welding machine.

11. The system of adjustable brackets according to claim 10, wherein the base includes indentations for identification and holding in a welding machine, arranged on the mesial, distal and gingival ends of the base.

12. The system of adjustable brackets according to claim 7, wherein the self-ligating clasp is a low-friction clasp.

13. The system of adjustable brackets according to claim 12, wherein the low-friction clasp is flat, and allowing the slot space to remain free.

14. The system of adjustable brackets according to claim 7, wherein the self-ligating clasp further includes an inner arm between the two lateral arms and joined to the connector; the inner arm having an irregular shape that is wider on its free end, in order to enter in the lower grooves of the bracket to avoid tilting; the connector having a thickening that serves as a stop when the clasp is inserted in the grooves.

15. The system of adjustable brackets according to claim 14, wherein the self-ligating clasp is a prescription-expressing clasp.

16. The system of adjustable brackets according to claim 15, wherein the prescription-expressing clasp has, in the middle portion of the inner arm, a curvature toward the lingual surface that forces an archwire to seat on the bottom of the slot, allowing the expression of the bracket prescription by using full size archwires.

17. The system of adjustable brackets according to claim 14, wherein the inner arm is wider than the lateral arms.

18. The system of adjustable brackets according to claim 17, wherein the self-ligating clasp is an esthetic clasp.

19. The system of adjustable brackets according to claim 18, wherein the esthetic clasp is manufactured in materials that allow the application of some color.

20. The system of adjustable brackets according to claim 7, further comprising a welding machine where the body and the base can be welded.

21. The system of adjustable brackets according to claim 20, wherein the welding machine is an electric welding machine.

22. The system of adjustable brackets according to claim 7, further including a measuring and programming devices to measure and program the inclination, angulation and rotation of the teeth of a patient.

23. The system of adjustable brackets according to claim 22, wherein the torque, the angulation and the rotation information is adjusted in order to program the prescription in accordance with the anatomic needs of each patient.

* * * * *